US005792900A

United States Patent [19]
Lee et al.

[11] Patent Number: 5,792,900
[45] Date of Patent: Aug. 11, 1998

[54] COMPOSITIONS AND METHODS FOR PRODUCING AND USING HOMOGENOUS NEURONAL CELL TRANSPLANTS

[75] Inventors: Virginia M.-Y. Lee; John Q. Trojanowski, both of Philadelphia, Pa.

[73] Assignee: The Trustees of the University of Pennsylvania, Philadelphia, Pa.

[21] Appl. No.: 640,894

[22] PCT Filed: Nov. 9, 1994

[86] PCT No.: PCT/US94/12899

§ 371 Date: Jun. 7, 1996

§ 102(e) Date: Jun. 7, 1996

[87] PCT Pub. No.: WO95/12982

PCT Pub. Date: May 18, 1995

Related U.S. Application Data

[63] Continuation of Ser. No. 150,368, Nov. 9, 1993, abandoned, which is a continuation-in-part of Ser. No. 911,980, Jul. 10, 1992, abandoned, which is a division of Ser. No. 780,715, Oct. 21, 1991, Pat. No. 5,175,103.

[51] Int. Cl.$^6$ .............................. C12N 15/00; C12N 5/06
[52] U.S. Cl. ...................... 800/2; 424/93.1; 424/93.2; 424/93.21; 424/93.7; 435/69.7; 435/70.1; 435/71.1; 435/172.3; 435/325; 435/368; 935/52; 935/70; 935/71; 935/99; 935/102
[58] Field of Search .......................... 435/240.2, 172.3, 435/320.1, 69.7, 325, 368, 70.1, 71.1; 424/93.1, 94.1, 93.2, 93.21, 93.7; 514/44; 800/2; 935/99, 102, 70, 71, 52

[56] References Cited

U.S. PATENT DOCUMENTS

| | | | |
|---|---|---|---|
| 4,892,538 | 1/1990 | Aebischer et al. | 604/891.1 |
| 5,175,103 | 12/1992 | Lee et al. | 435/172.3 |
| 5,180,820 | 1/1993 | Barde et al. | 536/23.51 |

OTHER PUBLICATIONS

Andrews P.W., "Pluriopotent Embryonal Carcionoma Clones Derived from the Human Teratocarcinoma Cell Line Tera-2," *Lab Invest.*, 1984, 50:147–162.

Andrews P.W., "Retinoic Acid Induces Neuronal Differentiation of a Cloned Human Embryonal Caarcinoma Cell Line in Vitro," *Devel. Biol.*, 1987, 103:285–293.

Abraham et al., "Increased PKA and PKC Activities Accompany Neuronal Differentiation of NT2/D1 Cells", *J. Neuronsci, Res.*, 1991, 28:29–39.

Andrews et al., "The expressionof MHC antigens by human teratocaarcinoma derived cell lines", *Tissue Antigens*, 1981, 17:493–500.

Backlund et. al., "Transplantation of adrenal nedullary tissue to striatum in parkinsonism", *J. Neurosurg.*, 1985, 62:169–173.

Cattaneo, E. et al., "Identifying and manipulating neuronal stem cells", *TINS*, 1991, 14:338–340.

Freed, C.A. et al., "Survival of Implanted Fetal Dopamine Cells and Neurologic Improvement 12 to 46 Months After Transplantation for Parkinson's Disease", *New Engl. J. Med.*, 1992, 327:1549–1555.

Fung K.-F. et al., "A Novel Modification of the Avidin–Biotin Complex Method for Immunohistochemical Studies of Transgenic Mice with Murine Monoclonal Antibodies", *J. Histochem. Cytochem.*, 1992, 40:1319–1328.

Kleppner et al., "Long-Term Survival and Maturation of Neurons Derived From the Human Cell Line N–tera 2 After Transplantation into Nude Mouse Brain", *Neuronsci. Abst.*, 1992, 18:782.

Lee et al., "Differentiation of NTERA–2 Clonal Human Embryonal Carcinoma Cells into Neurons Involves hte Induction of all Three Neurofilament Proteins," *J. Neuronsci.*, 1986, 6:514–521.

Lindvall et al., "Transplantation in Parkinson's Disease: Two Cases of Adrenal Medullary Grafts to the Putamen", *Ann. Neuronl.* 1987, 22:457–468.

Madrazo et al., "Open Microsurgical Augograft of Adrenal Medulla to the Right Caudate Nucleus in Two Patients with Intractable Parkinson's Disease", *New Engl. J. Med.*, 1987, 316:831–834.

Pleasure and Lee, "NTera 2 Cells: A Human Cell Line Which Displays Characteristics Expected of a Human Committed Neuronal Progenitor Cell", *J. Neuronsci. Res.* 1993, 35:585–602.

Pleasure et al., "Pure, Postmitotic, Polarized Human Neurons Derived from NTera 2 Cells Provide a System for Expressing Exogenous Proteins in Terminally Differentiated Neurons", *J. Neuronsci. Res.* 1992, 12:1802–1815.

Poltorak et al., "Human Cortical Neuronal Cell Line (HCN–1): Further In Vitro Characterization and Suitability for Brain Transplantation", *Cell Transplant*, 1992, I:3–15.

Renfranz, P.J. et al., "Region–Specific Differentiation of the Hippocampal Stem Cell Line HiB5 upon Implantation into the Developing Mammalian Brain", *Cell*, 1991, 66:713–729.

Snyder, E.Y. et al., "Multipotent Neural Cell Lines Can Engraft and Participate in Development of Mouse Cerebellum", *Cell*, 1992, 68:33–51.

Spencer, D.D. et al., "Unilateral Transplantation of Human Fetal Mesencephalic Tissue Into the Caudate Nucleus of Patients with Parkinson's Disease", *New Engl. J. Med.*, 1992, 327:1541–1548.

Trojanowski et al., "Medulloblastomas and Related Primitive Neuroectodermal Brain Tumors of Childhood Recapitulate Molecular Milestones in the Maturation of Neuroblasts", *Molec. Chem Neuropathol.*, 1992, 17:121–135.

(List continued on next page.)

*Primary Examiner*—Brian R. Stanton
*Attorney, Agent, or Firm*—Law Offices of Jane Massey Licata

[57] ABSTRACT

The invention concerns populations of homogenous, postmitotic human NT2N neurons that are useful for generating animal systems for study of neuron function. Also disclosed are methods of preparing animals that are useful for study of neurological function. In these methods, differentiated NT2N cells are stably implanted into host rodent animals.

11 Claims, 5 Drawing Sheets

OTHER PUBLICATIONS

Wiestler et al., "Retrovirus–Mediated Oncogene Transfer into Neural Transplants", *Brain Pathol.*, 1992, 2:47–59.

Widner, H. et al., "Bilateral Fetal Mesencephalic Grating in Two Patients with Parkinsonism induced by 1–Methyl–4–Phenyl–1,2,3,6–Tetrahydropyridine (MTPT)," *New Engl. J. Med.*, 1992, 327:1541–1563.

Younkin, et al., "Inducible expr4ession of neuronal glutamate receptor channels in the NT2 human cell line", *Proc. Natl. Acad. Sci. U.S.A.*, 1993, 90:2174–2178.

Emerich et al. Cell Transplantation vol. 1 pp. 401–427 (1992).

Orkin et al. Report and Recomendations . . . Gene Therapy, NIH. Dec. 7, 1995.

Friedman. Trends in Genetics 10(6): 210–214 (1994).

Trojanowski et al. Exp. Neurology 122: 283–294 (1993).

Spencer et al. The New England J. of Medicine 327(22): 1541–1548 (Nov. 26, 1992).

Shoushu et al. Nature 362: 450–453 (1993).

Freed et al. The New England J. of Medicine 327(22) 1549–1555. (Nov. 26, 1992).

Enfors. Proc. Natl. Acad. Sci. USA 86:4756–4760 (1989).

1

COMPOSITIONS AND METHODS FOR PRODUCING AND USING HOMOGENOUS NEURONAL CELL TRANSPLANTS

This application is a 371 of PCT/U.S. 94/12899, filed Nov. 9, 1994, published as WO95/12982 May 18, 1995, which is a continuation of application Ser. No. 08/150,368, filed Nov. 9, 1993, now abandoned, which is a continuation in part of application Ser. No. 07/911,980, filed Jul. 10, 1982, now abandoned, which is a divisional of U.S. application Ser. No. 07/780,715, filed Oct. 21, 1991, now U.S. Pat. No. 5,175,103.

FIELD OF THE INVENTION

The present invention relates to compositions useful for and methods of transplanting stable, homogeneous populations of neuron cells into non-human animals in order to generate non-human animal models useful to study human diseases, conditions and disorders. The present invention relates to compositions useful for and methods of transplanting stable, homogeneous populations of neuron cells into individuals in order to treat or prevent diseases, conditions and disorders, especially those characterized by loss, damage or dysfunction of the brain and/or loss, damage or dysfunction of an individuals neurons at other sites in the individual's body. This application is related to U.S. patent application Ser. No. 08/150,368 filed Nov. 9, 1993, U.S. patent application Ser. No. 08/170,668 filed Dec. 17, 1993, U.S. patent application Ser. No. 07/911,980 filed Jul. 10, 1992, and U.S. patent application Ser. No. 07/780,715, filed Oct. 21, 1991, now U.S. Pat. No. 5,175,103 issued Dec. 29, 1992, which are each incorporated herein by reference. This invention was made in the course of research sponsored by the NIH grant number NS18616. The United States Government has certain rights in this invention.

BACKGROUND OF THE INVENTION

The transplantation of major categories of central nervous system (CNS) cells (i.e. neurons, astrocytes) or CNS tissue fragments offers opportunities to study the developmental biology and immunological properties of these cells, to create animal models of CNS diseases such as Alzheimer's disease and to develop alternative strategies for the treatment of relentlessly progressive neurodegenerative disorders such as Alzheimer's disease, Parkinson's disease, Huntington's disease, amyotrophic lateral sclerosis and hereditary ataxia as well as to study other diseases, conditions and disorders characterized by loss, damage or dysfunction of neurons including transplantation of neuron cells into individuals to treat individuals suspected of suffering from such diseases, conditions and disorders. Indeed, recent pioneering efforts to utilize human fetal mesencephalic tissue grafts to ameliorate the extrapyramidal manifestations of drug induced and idiopathic Parkinson's disease emphasize the potential of transplanted human CNS tissues for the treatment of human neurodegenerative diseases (Freed, C. A., et al. 1992 *New Engl. J. Med.* 327:1549–1555; Spencer, D. D. et al. 1992 *New Engl. J. Med.* 327:1541–1548; and Widner, H., et al. 1992 *New Engl. J. Med.* 327:1556–1563). However, the results of these efforts have not been completely satisfactory.

The immortalization of CNS progenitor cells using constructs containing temperature sensitive promoters has enabled transplantation of genetically engineered precursors of neurons and glia, but brain grafts of these progenitors have given rise to mixed populations of glial and neuronal progeny (Cattaneo, E., and R. McKay 1991 *TINS* 14:338–340; Renfranz, P. J., et al. 1991 *Cell* 66:713–729; Snyder, E. Y., et al. 1992 *Cell* 68:33–51). An alternative strategy has been to use neuron-like transformed cell lines obtained from tumors of the CNS, but neoplastic neuron-like cells usually cannot be induced to permanently exit the cell cycle or they develop into tumors when transplanted into the rodent brain (Fung, K.-F. et al. 1992 *J. Histochem. Cytochem.* 40:1319–1328; Trojanowski, J. Q., et al. 1992 *Molec. Chem. Neuropathol.* 17:121–135; and Wiestler, O. D. et al. 1992 *Brain Pathol.* 2:47–59). A slowly dividing human neuronal cell line obtained from a child with unilateral megalencephaly was shown to exhibit a neuron-like phenotype in culture but grafts of these cells in the rodent CNS showed a mixture of neuronal and mesenchymal phenotypic properties (Poltorak, M., et al. 1992 *Cell Transplant* I:3–15).

There is a need for a method of generating animal models of CNS diseases and disorders by transplanting neurons into the brains of such animals to produce conditions which resemble or mimic CNS diseases, conditions or disorders.

There is a need for animal models of CNS diseases and disorders by transplanting neurons into the brains of such animals to produce conditions which resemble or mimic CNS diseases, conditions or disorders.

There is a need for a method of treating individuals suspected of suffering from CNS diseases, conditions or disorders by transplanting neurons in order to replace or introduce cells whose presence reverses or impedes the pathology associated with the disease being treated.

There is a need for a method of treating individuals suspected of suffering from neuron damage caused by stroke or injury such as head trauma, nerve injury or spinal injury by transplanting neurons in order to replace cells damaged by stroke or an injury.

SUMMARY OF THE INVENTION

The present invention relates to a method of treating an individual suspected of suffering from a disease, condition or disorder characterized by the damage or loss of neurons which comprises implanting a sample from a culture of at least 95% pure, stable, homogeneous post-mitotic human neurons into the individual at or near the site of the damage or loss.

The present invention relates to a method of treating an individual suspected of suffering from an injury, disease, condition or disorder to the Central Nervous System which comprises implanting a sample from a culture of at least 95% pure, stable, homogeneous post-mitotic human neurons into the individual's brain.

The present invention relates to a method of treating an individual suspected of suffering from an injury, disease, condition or disorder to the spinal cord which comprises implanting a sample from a culture of at least 95% pure, stable, homogeneous post-mitotic human neurons into the individual's spinal column.

The present invention relates to a method of treating an individual suspected of suffering from an injury, disease, condition or disorder to nerve cells which comprises implanting a sample from a culture of at least 95% pure, stable, homogeneous post-mitotic human neurons into the individual's body at the site of nerve dysfunction or damage.

The present invention relates to a pharmaceutical composition that comprises a sample from a culture of at least 95% pure, stable, homogeneous post-mitotic human neurons and a pharmaceutically acceptable medium.

The present invention relates to a method of generating a non-human animal model for a human disease, condition or disorder of the Central Nervous System comprising implanting a sample from a culture of at least 95% pure, stable, homogeneous post-mitotic human neurons into a non-human animal.

The present invention relates to an non-human animal comprising a sample from a culture of at least 95% pure, stable, homogeneous post-mitotic human neurons implanted in its brain, nervous system or spinal column.

DESCRIPTION OF DRAWINGS

FIG. 1A, FIG. 1B, FIG. 1C, FIG. 1D, FIG. 1E, FIG. 1F, FIG. 1G and FIG. 1H contain photomicrographs of NT2N graft in the hippocampus (dentate gyrus and polymorph layer) 4 weeks post-transplant probed with various monoclonal antibodies.

FIG. 2A, FIG. 2B and FIG. 2D show photomicrographs of three different NT2N grafts in the subcortical white matter and the dorsal diencephalon (FIG. 2C) 2–4 weeks post-transplant stained with Cresyl Violet (FIG. 2A, FIG. 2C and FIG. 2D) or the MAb (ED1) to macrophages (FIG. 2B).

FIGS. 1A–3H: FIG. 3A, FIG. 3B, FIG. 3C, FIG. 3D, FIG. 3E, FIG. 3F, FIG. 3G and FIG. 3H contain photomicrographs of an NT2N graft in the subcortical white matter at 4 weeks post-transplant probed with MAbs and counterstained with hematoxylin.

DETAILED DESCRIPTION OF THE INVENTION

Figure 1A:
FIGS. 1A–1H.

The present invention relates to compositions and methods relating to transplanting neurons into either individuals who are suspected of suffering from an injury, disease, disorder or condition or into non-human animals to generate a non-human animal model of a human disease, disorder or condition. The neurons used in the methods of the present invention are at least 95% pure, stable, homogeneous post-mitotic human neurons. Optionally, the neurons may be comprise exogenous genetic material. The neurons used in the methods of the present invention are genotypically and phenotypically homogenous.

As used herein, the term "sample" is meant to refer to one or more cells. In preferred embodiments, a sample contains a plurality of cells. According to the present invention, a sample from a culture of at least 95% pure, stable, homogeneous post-mitotic human neurons is implanted into either a non-human animal or a human. Accordingly, the methods of the present invention relate to the implantation of one or more cells from a culture of at least 95% pure, stable, homogeneous post-mitotic human neurons into either a non-human animal or a human.

As used herein, the term "at or near a site of said nerve damage" is meant to refer to the location where nerve cells are implanted in order to replace destroyed, damaged or dysfunctional nerve cells and/or restore function resulting from destroyed, damaged or dysfunctional nerve cells. The location is defined as being a site where such implanted cells can develop as replacement cells for destroyed, damaged or dysfunctional nerve cells and make the necessary linkages to restore function lost due to destroyed, damaged or dysfunctional nerve cells.

As used herein, the term "exogenous genetic material" refers to genomic DNA, CDNA, synthetic DNA and RNA, mRNA and antisense DNA and RNA which is introduced into the cell or an ancestor cell. The exogenous genetic material may be heterologous or an additional copy or copies of genetic material normally found in the individual or animal. When cells are used as a component of a pharmaceutical composition in a method for treating human injuries, diseases, conditions or disorders, the exogenous genetic material that is used to transform the cells may encode proteins selected as therapeutics used to treat the individual and/or to make the cells more amenable to transplantation. When cells are used in a method for generating non-human animal models of human CNS diseases or disorders, the exogenous genetic material that may be incorporated into the cells may encode proteins selected to create conditions in the non-human animal which simulates or resembles conditions in a human suffering from CNS disease, condition or disorder to be modeled.

The exogenous genetic material is preferably provided in an expression vector which includes the coding region of a protein whose production by the cells is desirous operably linked to essential regulatory sequences such that when the vector is transfected into the cell, the exogenous genetic material is capable of being expressed within the cell.

According to some embodiments of the present invention, a sample from a culture of pure, stable, homogeneous post-mitotic human neurons is transplanted into an individual being treated for a CNS injury, disease, condition or disorder. These cells essentially replace and/or function in place of endogenous damaged, dead, non-functioning or dysfunctioning cells. Thus, in the case of an individual suffering from an injury, disease, condition or disorder characterized by loss, damage or dysfunction of neurons such as, for example, diseases associated with nerve damage or spinal injury, the cells are transplanted into a site in the individual where the transplanted cells can function in place of the lost, damaged or dysfunctional cells and/or produce products needed to improve or restore normal functions that have been reduced or lost due to the lack of such products endogenously produced in the individual. In the case of an individual suffering from a CNS injury, disease, condition or disorder characterized by loss, damage or dysfunction of neurons in the brain, the cells are transplanted into the brain of the individual. The transplanted cells function in place of the lost, damaged or dysfunctional cells and/or produce products needed to improve or restore normal brain functions that have been reduced or lost due to the lack of such products endogenously produced in the individual.

According to some embodiments of the present invention, a sample from a culture of pure, stable, homogeneous post-mitotic human neurons are transplanted into the individual being treated for a disease, condition or disorder in order to provide living neurons which produce desired substances. The transplanted cells may produce specific products that, when present at or near the site of implantation in the treated individual, reverses or impedes the pathology associated with the disease, condition or disorder being treated.

According to some embodiments of the present invention, a sample from a culture of pure, stable, homogeneous post-mitotic human neurons are transplanted into a non-human animal in order to provide a model for a human CNS disease, condition or disorder. The transplanted cells may produce products that result in the development of conditions which are similar to or mimic the pathology of a CNS disease or condition.

The method may be used to treat individuals suffering from injuries, diseases, conditions or disorders characterized by the loss, damage or dysfunction of endogenous cells. The method may be used to treat individuals suffering from stroke, spinal injury or other injuries, conditions or disorders associated with neuron damage or death. CNS diseases and disorders which may be treated by practicing the methods of the present invention include any disease of the CNS which is characterized by the loss, damage or dysfunction of endogenous cells, the symptoms of which may be reversed or reduced in severity by providing neurons that can replace such cells and produce products needed for proper function or needed to counteract the presence of compounds that are not normally present or present at abnormal levels. The present invention is useful for the treatment of progressive neurodegenerative disorders such as Alzheimer's disease, Parkinson's disease, Huntington's disease, amyotrophic lateral sclerosis and hereditary ataxia as well as neurological conditions such as strokes and nerve injuries. The present invention is useful to treat diseases by serving as a delivery system to produce and disseminate active proteins and other active compounds needed for proper brain function.

A pharmaceutical composition according to the present invention useful for treating individuals suffering from injuries, diseases, conditions or disorders characterized by the loss, damage or dysfunction of endogenous cells comprises a sample from a culture of pure, stable, homogeneous post-mitotic human neurons and a pharmaceutically acceptable medium. The neurons used in the present invention must be a stable, homogeneous culture of post-mitotic human neurons that is at least 95% pure. The neurons used in the present invention may be transfected with exogenous genetic material.

The exogenous genetic material used to transform the cells may encode proteins selected as therapeutics for delivery to the brain of the treated individual. Protein products encoded by transfected genetic material include, but are not limited to, those leading to production of neurotransmitters (e.g. tyrosine hydroxylase) as well as neurotrophic substances such as nerve growth factor (NGF), brain-derived neurotrophic factor (BDGF), basic fibroblast growth factor (bFGF) and glialderived growth factor (GDGF). In addition, tumor suppressor genes such as P53 and thrombospondin can be incorporated into the cells.

According to another embodiment of the present invention, a sample from a culture of pure, stable, homogeneous post-mitotic human neurons are transplanted into the brain of a non-human animal in order to generate a non-human animal model of a human CNS disease, condition or disorder. The presence of the cells bring about changes in the animal's brain such that animal develops features which resemble or mimic the characteristics of the human CNS diseases, conditions or disorders. The transplanted cells produce specific products that, when present in the brain of the animal, give rise to conditions which resemble or mimic the pathology associated with the disease being modeled. The cells used to generate the non-human animal models according to the present invention useful for treating CNS diseases comprises a sample from a culture of pure, stable, homogeneous post-mitotic human neurons and a pharmaceutically acceptable medium. The neurons used in the present invention must be a stable, homogeneous culture of post-mitotic human neurons that is at least 95% pure.

CNS diseases and disorders which may be modeled by practicing the methods of the present invention include any disease of the CNS which is characterized by endogenous dead, non-functioning or dysfunctioning cells, particularly those characterized by cells producing proteins not normally associated with the cells or producing normal proteins at abnormal levels. Thus, the transplantation into the brain of an animal of cell which produce proteins associated with a human CNS disease gives rise to conditions which resemble or mimic the characteristics associated with the pathology of the disease or disorder being modeled. The present invention is useful to generate non-human animal models of progressive neurodegenerative disorders such as Alzheimer's disease, Parkinson's disease, Huntington's disease, amyotrophic lateral sclerosis, hereditary ataxia, and motor neuron and Lewy body disease. Many different genes are implicated in these diseases such as normal and mutated amyloid precursor genes, genes encoding kinases, phosphotases, normal and mutated superoxide dismutase, neurofilament proteins and apolipoprotein 4. In addition, specific oncogenes responsible for certain types of cancer can be incorporated to generate animal models for such cancer using the NT2 derived cells.

In some embodiments of the present invention, the neurons used may be produced by a method described in U.S. Pat. No. 5,175,103 issued Dec. 29, 1992, which teaches a method for obtaining >95% pure postmitotic human neurons (termed NT2N cells) from a human teratocarcinoma cell line (termed NTera2/clone PI or NT2 cells); following treatment of the NT2 cells with retinoic acid (RA). In addition to providing a model system for a wide range of biochemical, molecular biological and morphological studies of neurons in vitro, the stable, homogeneous population of pure human neurons may be used in in vivo transplants in order to generate animal models of CNS diseases and disorders or they may be used in in vivo transplants into the brains of individuals suffering from CNS diseases or disorders as therapeutics/prophylactics to introduce neurons which are capable of producing products that reverse or impede the pathology associated with CNS diseases or disorders afflicting the individual.

The NT2 cell line is unique among all other teratocarcinoma cell lines that are capable of differentiating into neurons, glia and mesenchymal cells, because the NT2 cells appear to correspond to progenitor cells, the progeny of which are restricted to the neuronal lineage (Abramham, I. et al. 1991 *J. Neurosci. Res.* 28:29–39; Andrews, P. W., et al. 1981 *Tissue Antigens* 17:493–500; Andrews, P. W. et al 1984. 1984 *Lab. Invest.* 50 147–162; Andrews, P. W. 1987. *Devel. Biol.* 103:285–293; Kleppner, S. R., et al 1992 *Soc. Neurosci. Abst.* 18:782; Lee, V. M.-Y. and P. W. Andrews 1986 *J. Neurosci.* 6:514–521; and, Younkin, D. P. et al. 1993 *Proc. Natl. Acad. Sci. U.S.A.* 90:2174–2178). Further characterization of the NT2N cells has shown that these cells most closely resemble CNS neurons (Pleasure, S. J., and V. M. -Y. Lee. 1993 *J. Neurosci. Res.* In press; and Pleasure, S. J., et al. 1992. *J. Neurosci.* 12:1802–1815). The NT2N cells exhibit other interesting properties of CNS neurons, i.e. they express almost exclusively the 695 amino acid long amyloid precursor protein (APP), produce and secrete the β-amyloid or A4 (β/A4) peptide found in Alzheimer's disease amyloid plaques and bear glutamate receptor channels on their cell surface.

The neurons used in the present invention may be transfected with exogenous genetic material. If produced as described in U.S. Pat. No. 5,175,103, the neurons used in the present invention may be transfected with genetic material prior to induction of differentiation. Methods of transfection are well known and taught in the above-referenced patent. The exogenous genetic material used to transform the cells may encode proteins whose presence within cell of the brain are associated with human diseases, disorders or conditions. Protein products encoded by transfected genetic material include, but are not limited to, normal and mutated amyloid precursor, kinases, phosphotases, normal and mutated superoxide dismutase, neurofilament proteins and apolipoprotein 4 as well as neurotransmitters (e.g. tyrosine hydroxylase) and neurotrophic substances such as nerve growth factor (NGF), brain-derived neurotrophic factor (BDGF), basic fibroblast growth factor (bFGF) and glial-derived growth factor (GDGF).

The exogenous genetic material used to transfect the cells is preferably provided in a vector which includes essential regulatory sequences operably linked to coding sequences such that the transfected genetic material is capable of being expressed within the cell.

Expression vectors that encode exogenous genetic material comprise a nucleotide sequence that encodes a protein to be produced operably linked to regulatory elements needed for gene expression. Accordingly, incorporation of the DNA or RNA molecule into the neuron cell results in the expression of the DNA or RNA encoding the protein and thus, production of the protein.

The exogenous genetic material that includes the nucleotide sequence encoding the protein operably linked to the regulatory elements may remain present in the cell as a functioning episomal molecule or it may integrate into the cell's chromosomal DNA. Exogenous genetic material may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be introduced into the cell.

The necessary elements of an expression vector include a nucleotide sequence that encodes a protein and the regulatory elements necessary for expression of that sequence in the cells. The regulatory elements are operably linked to the nucleotide sequence that encodes the protein to enable expression. The nucleotide sequence that encodes the protein may be cDNA, genomic DNA, synthesized DNA or a hybrid thereof or an RNA molecule such as mRNA.

The regulatory elements necessary for gene expression include: a promoter, an initiation codon, a stop codon, and a polyadenylation signal. It is necessary that these elements be operable in the neurons. Moreover, it is necessary that these elements be operably linked to the nucleotide sequence that encodes the protein such that the nucleotide sequence can be expressed in the neuron cells and thus the protein can be produced.

Initiation codons and stop codon are generally considered to be part of a nucleotide sequence that encodes the protein. However, it is necessary that these elements are functional in the neurons.

Similarly, promoters and polyadenylation signals used must be functional within the neuron cells.

Examples of promoters useful to practice the present invention include but are not limited to cytomegalovirus promoter, particular the immediate early promoter, SV40 promoter and retroviral promoters.

An examples of polyadenylation signals useful to practice the present invention includes but is not limited to SV40 polyadenylation signal.

An additional element may be added which serves as a target for cell destruction if it is desirable to eliminate transplanted cells for any reason. An expressible form of a herpes thymidine kinase (tk) gene can be included in the exogenous genetic material. When the exogenous genetic material is introduced into the neuron, tk will be produced. If it is desirable or necessary to kill the transplanted cells, the drug gangcyclovir can be administered to the individual and that drug will cause the selective killing of any cell producing tk. Thus, a system can be provided which allows for the selective destruction of transplanted cells.

In order for exogenous genetic material in an expression vector to be expressed, the regulatory elements must be operably linked to the nucleotide sequence that encodes the protein. Accordingly, it is necessary for the promoter and polyadenylation signal to be in frame with the coding sequence. In order to maximize protein production, regulatory sequences may be selected which are well suited for gene expression in the neuronal cells. Moreover, codons may be selected which are most efficiently transcribed in the cell. One having ordinary skill in the art can produce exogenous genetic material as expression vectors which are functional in neurons.

Neurons may be transplanted into individuals suspected of suffering from injuries, diseases, conditions or disorders characterized by the damage or loss of neurons at the site of such neuron injury or loss by direct grafting of neurons at the site of neuron injury or loss. Neurons may be transplanted into the brains of individuals suspected of suffering from CNS diseases, conditions or disorders by direct grafting of neurons into the brains of such individuals. Additionally, neurons may be transplanted into the brains of individuals suffering form head trauma or strokes. Individuals suspected of or identified as suffering from diseases, conditions, disorders, or injuries rendering neurons in the brain damaged, destroyed or dysfunctional may be treated by implantation of neurons to replace or compensate for the loss of neuron function due to the destruction or dysfunction of endogenous neurons.

In some embodiments, $1 \times 10^3$ to $1 \times 10^6$ neurons are implanted. In some embodiments, $5-10 \times 10^4$ neurons are implanted. Two techniques have been used for neural transplantation, the first comprises stereotaxic surgery in which a neuron cell suspension is implanted into the brain, the second in which the cells are grafted into the brain by microsurgery. Techniques for transplanting neural tissue are disclosed in: Backlund, E.-O. et al., (1985) *J. Neurosurg.* 62:169–173; Lindvall, O. et al. (1987) *Ann. Neurol.* 22:457–468; and Madrazo, I. et al. (1987) *New Engl. J. Med.* 316:831–834; each of which is incorporated herein by reference.

Neurons may be implanted into the spinal cord at or near the site of nerve damage from disease or injury. The implanted cells further differentiate into motor neurons, thereby replacing or reconnecting nerves at the site of damage. In some embodiments, the injury is to a motor neuron which is part of the spinal cord. In some embodiments, the injury is to a motor neuron outside the spinal column. Neurons of the invention are implanted at the site of the nerve cell injury, i.e. in proximity to the injured cell or cells at a location where differentiation of implanted cells can replace nerve function and reconnect nerves of the individual to remedy or otherwise ameliorate the injury. The neurons are implanted in a location that allows processes which develop therefrom to substitute for the processes of the damaged nerve, thereby repairing the damaged nerve network.

Neurons may be transplanted into the brains of nonhuman human animals by injection of neurons into one hemisphere using a stereotaxic instrument and a hand-held 10 ml Hamilton syringe. Aliquots of $1\times10^3$ to $1\times10^6$ neurons are injected into the adult and neonatal rats. In some embodiments, $5-10\times10^4$ neurons are injected. For the adult rats, cells are injected stereotaxically into cerebral cortex, subjacent white matter or hippocampus at one site in a single hemisphere of each rat.

The present invention is further illustrated by the following examples, which are not intended to be limiting in any way.

EXAMPLES

Example 1

Studies of NT2N cells transplanted into the brains of nude mice show that these NT2N cells integrate as neurons into the brains of immunodeficient nude mice where they survive >12 months without evidence of rejection or tumor formation. Furthermore, the transplantation of NT2N neurons in cyclosporine-treated and untreated immunocompetent Sprague-Dawley rats has been performed and survival of the cells has been observed.

The following is a review of experiments demonstrating implantation of transfected neuronal cells into immunocompetent animals.

Materials and Methods

Culture of NT2 cells and generation of NT2N neurons were performed essentially as described in U.S. Pat. No. 5,175,103. Briefly, NT2 cells were cultured using standard techniques and were passaged 1:3 twice per week in Opti-MEM with 5% fetal bovine serum and penicillin/streptomycin. NT2 cells were induced to differentiate into neurons by administration of 10 μm retinoic acid (RA), which was replenished twice weekly, for 5 weeks at which time the cells were replated to establish Replate 1 cells. Highly differentiated NT2N cells were then obtained following two subsequent replate manipulations (designated Replate 2 and Replate 3) at which time the NT2N cells were >99% pure. Freshly harvested aliquots of Replate 3 NT2N neurons were washed three times in buffer and then used in the transplantation studies described here.

Additionally, in experiments conducted in 2 rats, previously frozen aliquots of NT2N cells were thawed immediately prior to injection into the CNS.

Implantation of NT2N Cells Into Rat Brain

Adult (170–280 gm) female Sprague/Dawley rats were anesthetized by intraperitoneal injections of Ketamine (87 mg/kg) and Xylazine (13 mg/kg), prepared for surgery and placed in a stereotaxic instrument (Kopf, Tujunga, Calif.). Neonatal (postnatal day 5) female Sprague/Dawley rats were anesthetized by hypothermia during the injection of NT2N cells into one hemisphere using a stereotaxic instrument and a hand-held 10 μl Hamilton syringe. Aliquots of $5-10\times10^4$ NT2N cells were injected into the adult and neonatal rats. For the adult rats, NT2N cells were injected stereotaxically into cerebral cortex, subjacent white matter or hippocampus at one site in a single hemisphere of each rat. A total of 68 rats were used in this study (see Table 1).

The stereotaxic injection sites were determined using system B of Pellegrino et al. (Pellegrino, L. J., et al. 1979. *A Stereotaxic Atlas Of The Rat Brain*, Plenum Press, New York) and all of the injections were performed by injecting 2 μl of a suspension of the NT2N cells over 5 min. After the injection, the needle was left in place for another 5 min. and then slowly removed. The viability of the NT2N cells before they were injected was monitored microscopically using Trypan blue exclusion. Similar procedures were used to monitor the viability of residual, uninjected NT2N cells after the transplantation procedure had been completed.

A subset of the adult rats (N=13) implanted with NT2N cells were treated daily by the oral (N=8; using a gauvage tube) or subcutaneous (N=5) administration of cyclosporine (7–10 mg/kg per day) for the duration of their survival post-transplantation.

Following different post-transplantation survival times, the rats were deeply anesthetized and sacrificed by perfusion with phosphate buffered saline (to wash out red blood cells and serum proteins) followed by 70% ethanol and 150 mM NaCl. The brains were removed and fixed by overnight immersion in 70% ethanol and 150 mM NaCl. The post-transplant survival times ranged from 4 days to 21 weeks as summarized in Table 1.

Table 1 summarizes data on the number of adult (with and without subcutaneous or oral cyclosporine treatment) and neonatal rats used for transplantation as well as the survival times post-transplantation for each group of rats (left and middle columns). The number of rats with viable NT2N grafts is shown in the far right column. The number of rats treated with subcutaneous (sc) cyclosporine is indicated in parentheses. Immunohistochemical Procedures:

The methods for tissue processing and light microscopic immunohisto-chemical analysis are well known. Antibodies were used for the immunohistochemical characterization of the NT2N grafts. Both monoclonal and polyclonal antibodies to neuronal and glial cytoskeletal proteins and other polypeptides that have been shown to serve as molecular signatures of the neuronal or glial phenotype were selected to identify and characterize the NT2N grafts. These antibodies have been extensively characterized and their properties are summarized in Table 2.

Specifically, Table 2 summarizes the properties of the 27 different antibodies used in this study and their reactivity with NT2N cells grafted into the rat brain. The far left column indicates the polypeptide recognized by the antibody which is named in the second column. The third column gives the dilution or immunoglobulin concentration of each antibody as it was applied here. The fourth column indicates whether or not the antibody stained grafted NT2N cells (+ positive; −negative; ±-weak or equivocal staining). The antibodies are grouped together according to the cell types in which they are predominantly or exclusively expressed.

The abbreviations used in the first column of the Table 2 (in alphabetical order) are:

GFAP =Glial fibrillary acid protein;

MAP2=Microtubule-associated protein 2;

MAP5=Microtubule-associated protein 5;

MBP=myelin basic protein;

N-CAM=Neural-cell adhesion molecule;

NF=Neurofilament;

NF-L=Low molecular weight NF protein;

NF-M=Middle molecular weight NF protein;

NF-H=High molecular weight NF protein;

p75 NGFR=Low affinity (75 kD) nerve growth factor receptor;

$P^{ind}$=Phosphate independent epitope in NF-L or NF-H;

$P^-$=Non- or poorly phosphorylated epitope in NF-H or NF-M;

$P^+$=Moderately phosphorylated epitope in NF-H;

$P^{+++}$=Heavily phosphorylated epitope in NF-H;

PHF=Paired helical filaments in Alzheimer's disease neurofibrillary tangles.

Note that two antibodies (i.e. T3P and PHF1) to tau proteins recognize fetal tau and the abnormally phosphorylated tau proteins (at serine number 396 according to the numbering system for the 441 amino acid long tau protein) in PHFs (also known as A68 proteins), but not normal adult tau. Note that although the anti-CFAP and anti-macrophage MAbs stained occasional reactive astrocytes and macrophages, respectively, that had infiltrated the graft, the NT2N cells themselves were not stained by these MAbs.

RESULTS

Specific Identification Of NT2N Grafts With Monoclonal Antibodies

Figure 1B:
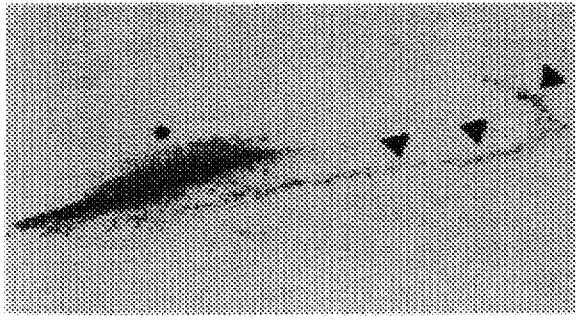
Figure 1C:
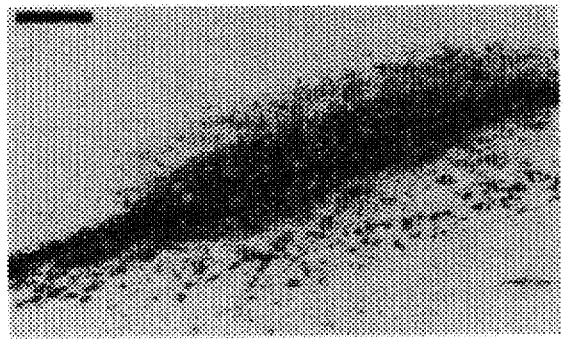
Figure 1D:
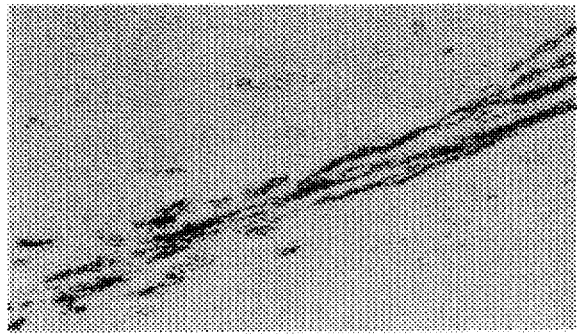
Figure 1E:
Figure 1F:
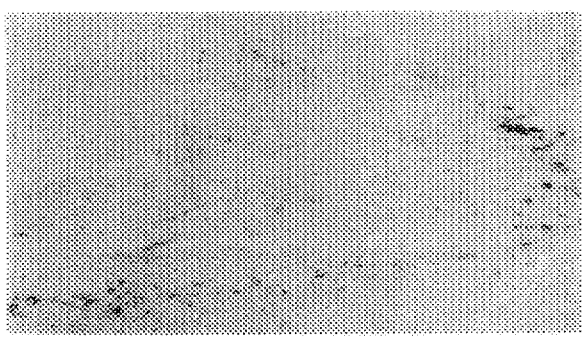
Figure 1G:
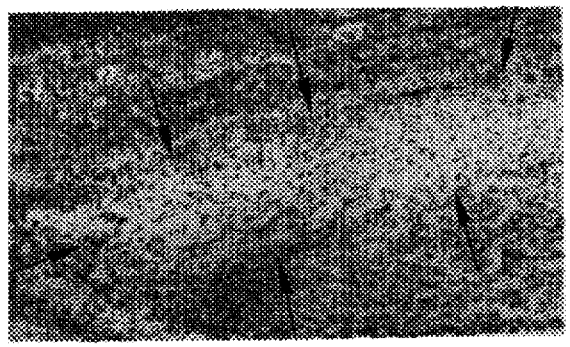
Figure 1H:
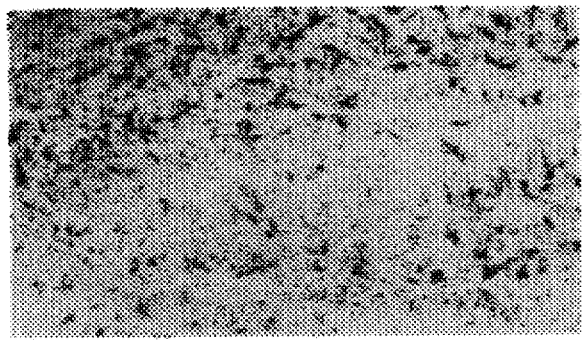

FIG. 1A and FIG. 1B contains photomicrographs of NT2N graft in the hippocampus (dentate gyrus and polymorph layer) 4 weeks post-transplant. FIG. 1A shows a low power view of a Cresyl Violet stained section of the NT2N graft (delineated by the arrows). FIG. 1B shows a low power view of the same NT2N graft stained with the human specific anti-N-CAM MAb (MOC 1). The asterisk lies above the portion of the graft containing the perikarya and simple dendritic arbor of the NT2N neurons while the arrow heads identify the axons emanating from the graft and extending in the mossy fiber pathway dorsal to pyramidal neurons in CA3. The region identified by the asterisk is shown at higher power in FIG. 1C and the segment of graft-derived axons located below the middle arrow head is shown at higher power in FIG. 1D. Note that only the NT2N neurons and their processes are stained by this MAb. FIG. 1A and FIG. 1B are at the same magnification and the bar in FIG. 1A=100 µm. FIG. 1C and FIG. 1D show a higher power views of the NT2N graft stained by the human specific anti-N-CAM MAb (MOC1). Note that the NT2N neurons and some of their dendrites (FIG. 1C) as well as their axons (FIG. 1D) are stained, but not the endogenous rodent N-CAMs. The photomicrographs in FIG. 1C, FIG. 1F, FIG. 1G and FIG. 1H are all at the same magnification and the bar in FIG. 1C=100 µm, while FIG. 1D and FIG. 1E are taken at a slightly higher magnification and the bar in FIG. 1C corresponds to 25 µm in FIG. 1D and FIG. 1E. FIG. 1E and FIG. 1F show regions similar to those illustrated in FIG. 1C and FIG. 1D, respectively, in an adjacent section stained with the MAb RHdO20 (FIG. 1D) to poorly phosphorylated NF-H/M and the MAb HO14 (FIG. 1F) to moderately phosphorylated isoforms of NF-H. FIG. 1G shows results obtained with a MAb to highly phosphorylated NF-H (RMO24) which stains only endogenous rat axons, but not the NT2N graft (arrows) despite the fact that RMO24 also recognizes human NF-H. The section shown in FIG. 1H is adjacent to that seen in FIG. 1F and it was probed with the MAb to GFAP. Some reactive astrocytes infiltrate the graft similar to the colonization of dorsal root ganglion grafts transplanted into rat brain, but most CFAP positive reactive astrocytes surround the graft. The sections in FIG. 1B–FIG. 1H were lightly counterstained with hematoxylin.

Figure 2A:
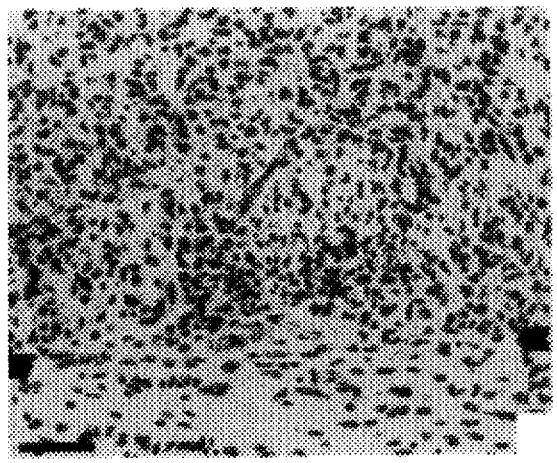
FIGS. 2A–2D.
Figure 2B:
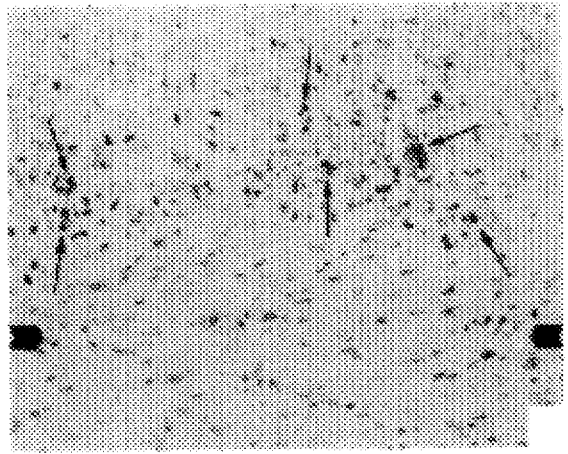
Figure 2C:
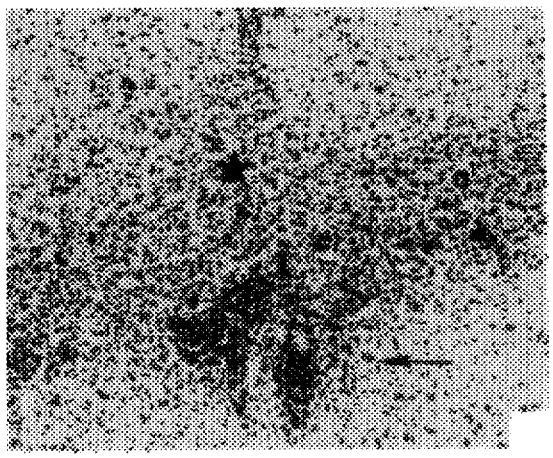
Figure 2D:
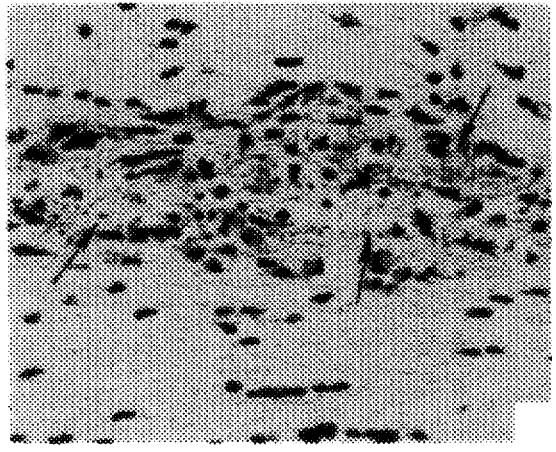

FIG. 2A, FIG. 2B, FIG. 2C and FIG. 2D show photomicrographs of three different NT2N grafts in the subcortical white matter (FIG. 2A, FIG. 2B and FIG. 2D) and the dorsal diencephalon (FIG. 2C) 2–4 weeks post-transplant stained with Cresyl Violet (FIG. 2A, FIG. 2C and FIG. 2D) or the MAb (ED1) to macrophages (FIG. 2B). FIG. 2A and FIG. 2B are adjacent sections of the same graft and the arrow heads identify the interface between the graft (above) and the subjacent white matter (below). FIG. 2A and FIG. 2B are at the same magnification and the bar in FIG. 2A=50 µm. The arrows in FIG. 2B identify ED1 positive macrophages in an area of the graft containing some NT2N neurons undergoing focal karyorrhexis. More extensive inflammation is seen around blood vessels in FIG. 2C (arrow) at the margin of the graft (star) while more severe karyorrhexis of grafted NT2N cells is seen in another subcortical white matter NT2N graft shown in FIG. 2D where the arrows identify accumulations of nuclear debris. FIG. 2C and FIG. 2D are at different magnifications and the bar in FIG. 2A corresponds to 100 µm in FIG. 2C and to 30 µm in FIG. 2B.

Figure 3A:
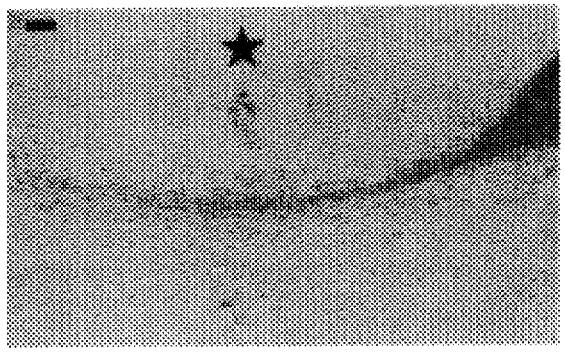
Figure 3B:
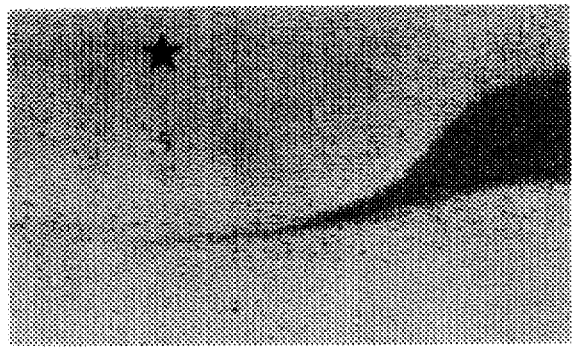
Figure 3C:
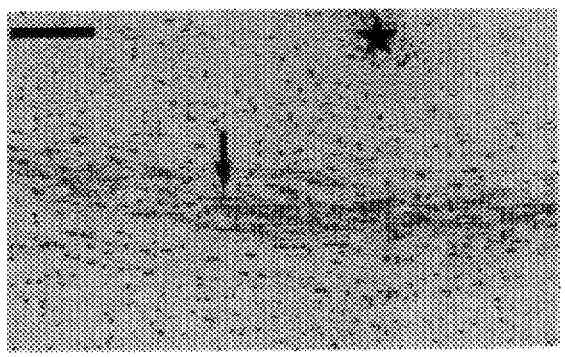
Figure 3D:
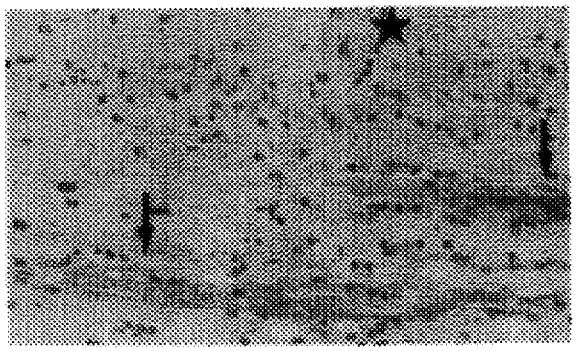
Figure 3E:
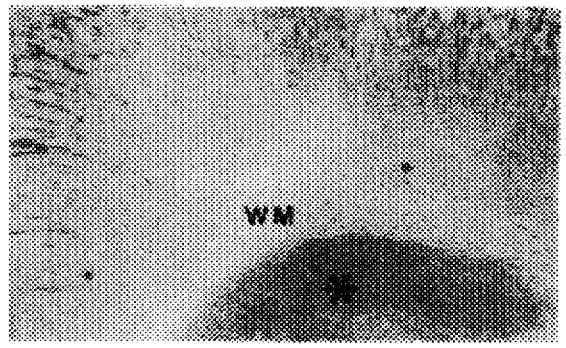
Figure 3F:
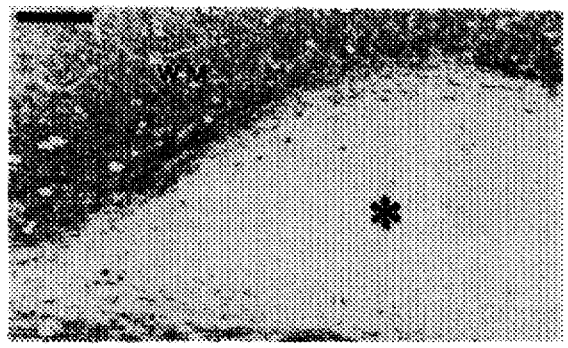
Figure 3G:
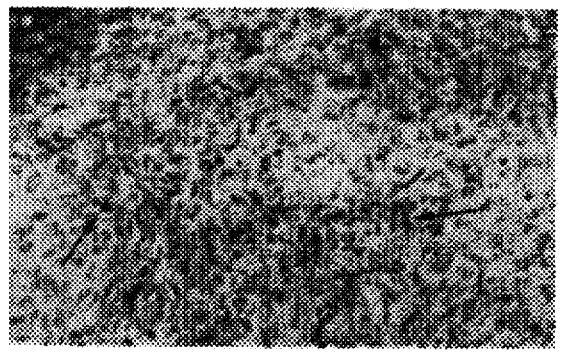
Figure 3H:
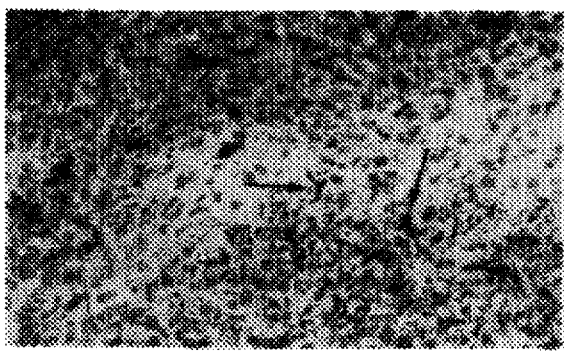

FIG. 3A, FIG. 3B, FIG. 3C, FIG. 3D, FIG. 3E, FIG. 3F, FIG. 3G and FIG. 3H contain photomicrographs of an NT2N graft in the subcortical white matter at 4 weeks post-transplant probed with MAbs and counterstained with hematoxylin. The section shown in FIG. 3A was stained with the human specific anti-NF-H MAb (H014) which demonstrates the grafted perikarya and their dendrites in the NT2N transplant to the right in the figure. Labeled axons extend medially from the graft site to the left in this panel. Note that these axons cross the midline (star) within the corpus callosum. The section in FIG. 3B, which was a section adjacent to that shown in FIG. 3A, was probed with a MAb to human N-CAM (MOCL) which stains the somatodendritic domain of NT2N cells in the graft to the right in this figure as well as axons that cross the midline (star) to the left within the corpus callosum. FIG. 3A and FIG. 3B are at the same magnification and the bar in FIG. 3A=100 µm. The axons in the corpus callosum seen in FIG. 3A and FIG. 3B are shown at higher power in FIG. 3C and FIG. 3D, respectively. These axons (arrows in FIG. 3C and FIG. 3D) cross the midline (star in FIG. 3C and FIG. 3D) to the hemisphere contralateral to the NT2N graft. FIG. 3C and FIG. 3D are at different magnifications and the bar in FIG. 3C=100 µm while the same bar corresponds to 50 µm in FIG. 3D. In FIG. 3E, the MAb to MAP2 (AP14) labels the somatodendritic domain of the grafted NT2N neurons. The cell body mass of the graft is identified by an asterisk and the overlying white matter (WM) is unstained. The somatodendritic domain of endogenous host neurons in the overlying cortex also are labeled in this section and labeled apical dendrites are most prominent at this magnification. FIG. 3E is at the same magnification as FIG. 3A and FIG. 3B. In FIG. 3F, the MAb to highly phosphorylated NF-H (RHO24) does not stain the NT2N neurons and their processes in the graft (asterisk). However, endogenous axons in the surrounding white matter (WM) are labeled by this MAb thereby delineating the extent of the cell body mass and dendrites of this graft. The bar in FIG. 3F=100 µm. The two photomicrographs shown in FIG. 3G and FIG. 3H are high power views of the NT2N grafts in adjacent sections stained with the anti-NF-L antiserum (FIG. 3G) and the MAb (TA51) to moderately phosphorylated isoforms of NF-H (FIG. 3H). Note that many of the NT2N neurons contain immunoreactive NF-L and NF-H (arrows in FIG. 3G and FIG. 3H, respectively) in their perikarya and processes. Additionally, endogenous rodent axons in the white matter (upper left in FIG. 3G and FIG. 3H) also are labeled by these antibodies. FIG. 3G and FIG. 3H are at the same magnification and the bar in FIG. 3F corresponds to 50 µm in FIG. 3G and FIG. 3H.

Although the grafts could be recognized in Cresyl Violet stained sections (FIG. 1A, FIG. 2A, FIG. 2B and FIG. 2D), the identification of transplanted NT2N cells in the rodent CNS was greatly facilitated by exploiting the restriction of certain polypeptides or epitopes contained within some of these polypeptides to human versus rat and mature versus immature CNS neurons. For example, MOCl, the monoclonal antibody (MAb) to human neural cell adhesion molecules (N-CAMs), was shown to recognize N-CAMs in the human NT2N neurons, but not the N-CAMs in the rat CNS (FIG. 1B–FIG. 1D). Indeed, the cytology of the NT2N cells was not sufficiently distinctive to allow recognition of the NT2N cells without the use of immunohistochemistry. Furthermore, axons arising from the NT2N grafts were only identifiable as graft derived when they were labeled with the human polypeptide specific antibodies described here (FIG. 1B, FIG. IF, FIGS. 3A–3D). In addition to the anti-N-CAM MAb, the grafted NT2N cells also could be specifically identified with the MAb H014, an antibody that recognizes moderately phosphorylated isoforms of the middle (NF-M) molecular weight (Mr) neurofilament (NF) subunit in the human CNS and in NT2N cells, but not in the rodent CNS (FIG. 1F). In contrast, RMO24 (FIG. 1G) and RMO217, both of which are MAbs to the most heavily phosphorylated isoforms of the high (NF-H) Mr NF subunit that appear only in mature CNS neurons, immunostained NF-H in rodent CNS neurons, but these MAbs did not stain the human NT2N cells in the grafts described here. The inability of RMO24 and RMO217 to stain the grafted NT2N cells probably reflects the incomplete phosphorylation of NF-H in the grafted NT2N cells (which reflects the incomplete maturation of these grafted neurons), since both MAbs recognize phosphorylated NF-H extracted from the fully mature, human CNS. If the NT2N cells are allowed to survive for an extended period of time (i.e. >6 months) in the immunodeficient nude mouse brain, then the grafted NT2N neurons acquire the most heavily phosphorylated isoforms of NF-H and these fully mature grafted neurons are labeled by RMO24 and RMO217. However, grafted NT2N cells were only studied here for post-transplant survival times of <4 months, and both RMO24 and RMO217 strongly stained rat CNS neurons, but not the grafted NT2N cells, and MOC1 and HO14 stained the NT2N grafts specifically and intensely, but not rat CNS neurons or other rat CNS cells. Thus, all 4 of these MAbs were used to screen sections from all 68 rats that received implants of the NT2N cells in order to specifically identify the surviving NT2N grafts. Additionally, a MAb (2.2B10) to glial fibrillary acidic protein (GFAP) stained reactive astrocytes surrounding the graft (FIG. 1H) which also helped to delimit the NT2N grafts. Some of these reactive astrocytes infiltrated the NT2N grafts (FIG. 1H) similar to the colonization of dorsal root ganglion grafts by reactive astrocytes transplanted into the rat brain. Screening the graft sites with this panel of MAbs provided a highly effective strategy for identifying grafted NT2N cells even when they existed as small clumps trapped in needle tracninges or in the needle track dorsal to the injection site. Survival Of Grafted NT2N Cells:

Nearly all of the transplanted NT2N cells were accurately implanted into neocortex, subjacent white matter and hippocampus although a few also were detected in the diencephalon, the lateral ventricle or within the leptomeninges overlying the neocortical injection site. The number and disposition of the grafted NT2N cells varied from rat to rat, but NT2N grafts were identified immunohistochemically in 100% of adult (N=5) and neonatal (N=5) rats that survived for up to 2 weeks without cyclosporine treatment (see Table 1 for a summary of these and the following data on NT2N graft survival). This group of rats with viable NT2N grafts included 2 rats treated with cyclosporine that had been implanted with aliquots of previously frozen NT2N cells. At the next post-transplant survival interval, i.e. 4 weeks, 10/24 adult and 2/2 neonatal rats that were not treated with cyclosporine contained NT2N brain grafts (Table 1), and many of the transplanted cells resembled small stellate neurons morphologically and histochemically in Nissl stained preparations of the grafts. However, at subsequent post-transplant survival times, only 1 of 19 adult or neonatal rats that were not treated with cyclosporine contained identifiable, surviving NT2N neurons. These findings reflect rejection of the NT2N grafts rather than the cessation of expression of N-CAMs and NF proteins by the grafted NT2N cells. This conclusion is based upon 4 reasons:

1) inflammatory cells were detected in some of the viable grafts in association with cellular debris as early as 2 weeks post-transplantation (FIG. 2C) and many of these inflammatory cells were identified as macrophages using the macrophage specific ED1 MAb (FIG. 2B);

2) cyclosporine prolonged the survival of all NT2N grafts in rats that received this agent by a subcutaneous route;

3) the maximum number of macrophages and inflammatory cells were noted to infiltrate the graft site at 2–4 weeks post-transplantation; and 4) in the immuno-deficient nude mouse, grafted NT2N cells survive >12 months, continue to express N-CAMs and NF proteins, and progressively mature such that they acquire a fully mature neuronal phenotype by 12 months post-transplant.

Of the 5 rats that received subcutaneous cyclosporine, all 5 contained viable NT2N grafts at post-transplant intervals that ranged from 2 to 12 weeks. In contrast, administration of cyclosporine by gauvage at the same dose (i.e. 7–10 mg/kg) appeared less effective in preventing graft rejection since only 2 of 8 rats treated in this manner contained an identifiable NT2N graft (Table 1). Notably, the administration of cyclosporine to these rats did not appear to have any detectable effect on the ability of the surviving NT2N cells to express a range of neuronal polypeptides. Maturation Of Grafted NT2N Cells And The Establishment Of Neuronal Polarity:

Presumably, as a result of their progressive maturation in vivo, NT2N grafts that survived 2–4 weeks post-transplantation were the largest and the most amenable to serial section immunohistochemical analysis, while only a limited number of sections containing identifiable NT2N cells could be obtained from rats that survived 4 days to 1 week post-transplantation. For this reason, studies were focused on the maturational state and polarity of the NT2N cells on rats that survived 2–4 weeks post-transplantation. At these time points, NT2N cells in hippocampus or in the subcortical white matter (which consistently contained larger populations of NT2N cells than the neocortex perhaps due to leakage of the NT2N cells from the cortical injection site into the overlying subarachnoid space) expressed several well characterized polypeptides (e.g. NF subunits and other neuronal cytoskeletal proteins, synaptic polypeptides) that unequivocally identified the NT2N cells as neurons (see FIGS. 3A–3E, FIG. 3G, FIG. 3H and Table 2). However, these neurons resembled late fetal human spinal cord (i.e. >25 weeks gestational age) or young postnatal human cerebellar (i.e. <1 year old) neurons rather than fully mature neurons of the adult CNS in that they failed to acquire heavily phosphorylated isoforms of NF-H. In contrast, polypeptides expressed by glial cells were infrequent in these grafts and the presence of rare GFAP positive astrocytes in these grafts (FIG. 1H) undoubtedly reflects the migration of reactive rat astrocytes into the grafts.

Four week old NT2N neurons extended axons over several millimeters (FIGS. 1B–1F), and some of these axons projected to the hemisphere contralateral to the graft site (FIGS. 3A–3D). Although dendrites were readily identified because they could be labeled with antibodies to microtubule associated proteins (MAPs) restricted to the somatodendritic domain (e.g. MAP2), these dendrites were short with a simplified branching pattern (FIG. 3E). Nonetheless, the presence of identifiable axons and dendrites containing polypeptides that were compartmentalized like their counterparts in authentic rat or human neurons in vivo (FIGS. 1B–1F and FIGS. 3A–3E, FIG. 3G and FIG. 3H) indicate that by 4 weeks post-transplantation the grafted NT2N neurons had acquired the molecular phenotype and structural polarity seen in nearly mature human CNS neurons in vivo. Further, none of the grafted NT2N cells expressed proteins (e.g. nestin, vimentin, p75 NGFR) that are found in neuronal progenitor cells or very immature (i.e. "nascent" ) human CNS neurons. Significantly, despite evidence of neuronal degeneration due to graft rejection (FIGS. 2A–2D), none of the grafts showed evidence of neuronal cytoskeletal protein abnormalities similar to those seen in common neurodegenerative diseases. Finally, there was no evidence (e.g. mitoses, metastases) to indicate that any of the surviving NT2N cells reverted to a neoplastic phenotype.

DISCUSSION

This study demonstrates the properties of CNS transplants of pure populations of clonal human neuron-like cells that are capable of undergoing progressive, normal maturation and integration into the host mammalian brain without evidence of tumor formation. Only one other CNS cell line, the human HCN-1 line, appears to exhibit an exclusive in vitro commitment to the neuronal lineage, but this cell line does not maintain a stable neuronal phenotype when transplanted into the CNS of experimental animals (Ronnett, C. V. et al. 1990 *Science* 248:603–605).

The paucity of suitable neuronal cell lines for transplantation has limited studies of the immunological response of the CNS to transplanted neurons alone. This report demonstrates that the NT2N neurons are capable of expressing antigens that induce rejection by about 4 weeks post-transplant. Although the precise nature of these antigens in the NT2N cells is unknown at this time, human teratocarcinoma cell lines similar to the NT2 parent cell line have been shown to express major histocompatibility antigens such as HLA-A, B and C antigens and $\beta_2$ microglobulin.

More significantly, this study demonstrates that transplanted NT2N neurons are capable of undergoing partial neuronal maturation in the rat brain. The NT2N cells injected into the rat brain progressively matured to about the same extent as their in vitro counterparts maintained in culture for up to 28 days following Replate 3. However, they did not attain the same level of maturity as transplanted NT2N cells that survived for >9–12 months in the immunodeficient nude mouse brain. Specifically, the NT2N grafts in the rat brain did progress to a level of maturation by 4 weeks post-transplant that corresponded to the maturational state of authentic human neurons in the late embryonic spinal cord or in the immature, young postnatal cerebellum. They differ significantly from olfactory sensory neurons and the neuron-like tumor cells in CNS medulloblastomas. However, the transplanted and cultured NT2N cells do resemble the differentiated and fairly mature neurons that have been observed in situ in some teratocarcinomas and many teratomas.

Based on the findings presented here, the transplantation of the NT2N cells into experimental animals can be exploited for several types of unique studies of the developmental biology of neurons and the regressive neurodegenerative events that occur in some neurological disorders. First, the ability to "re-start" the process of neuronal maturation and the development of neuronal polarity by transplanting the NT2N cells into different regions of the rodent brain can be used as models of these two important developmentally regulated processes. The availability of an effective human model system to study these processes in a controlled experimental setting should greatly facilitate efforts to gain insights into the regulatory mechanisms that govern these processes. This model system also will allow the opportunity to explore the possibility that the microenvironment of the host brain might induce NT2N cells grafted into different neuroanatomical sites to assume a region specific morphological and neurotransmitter phenotype.

Moreover, wild type or genetically modified NT2N cells can be used to develop animal models of humans diseases, conditions and disorders, particularly nervous system diseases. For example, the NT2N cells preferentially express the 695 amino acid long Amyloid precursor protein ($APP_{695}$) and they secrete the $\beta/A4$ peptide into the culture medium. Hence, the wild type NT2N cells, NT2N cells transfected to overexpress $APP_{695}$, or NT2N cells transfected to overexpress $\beta/A4$ can be transplanted in order to provide an animal model that releases $APP_{695}$ or $\beta/A4$ into the extracellular space following transplantation. The deposition of $\beta A4$ peptides that occur in the Alzheimer's disease brain can be modelled in this way.

Transplantation of NT2N cells genetically engineered to produce bioactive molecules can be used to develop novel methods to circumvent the blood-brain barrier for the treatment of human neurodegenerative diseases. For example, in view of the therapeutic promise evidenced by recent studies of the use of fetal mesencephalic grafts for the treatment of Parkinson's disease, induction of NT2N cells to acquire a dopaminergic phenotype for use in the treatment of Parkinson's disease followed by transplantation can be a therapy for individuals suspected of suffering from Parkinson's disease.

Example 2

Transfection and Staining for $\beta$-galactosidase

Highly purified populations of neurons from a human teratocarcinoma cell line were obtained as described in U.S. Pat. No. 5,175,103. When undifferentiated, the NT2 cells were transfected with 100 µg SPUD1 and 10 µg of pSV2neo by lipofection using LIPOFECTIN transfecting reagent (Bethesda Research Laboratories). SPUD1 is a $\beta$-galactosidase expression vector which utilizes the SV40 promoter and has Moloney murine leukemia virus long terminal repeats upstream and downstream. After two days in complete medium, the transfectants were selected with 200 µg/ml G418 (Gibco) for seven days. Cells were stained for $\beta$-galactosidase activity with 1 mg/ml X-gal, 5 mM potassium ferrocyanide, 5 mM potassium ferricyanide, 2 mM $MgCl_2$ in PBS after fixation in 2% paraformaldehyde, 0.2% glutaraldehyde in phosphate buffered saline pH 7.4. $\beta$-gal positive cultures were subcloned twice and the subclones were used for further studies. The cells were photographed using Hoffman modulation contrast to allow the simultaneous visualization of the blue reaction product and the processes.

The $\beta$-galactosidase ($\beta$-gal) expression plasmid was shown to be present in both undifferentiated and post-mitotic cells. Thus, transfection of expression plasmids into undifferentiated cells allows the introduction of exogenous genetic material into cells. The cells can then be induced to become stable, post-mitotic human neurons and can express the exogenous genetic material.

TABLE 1

POST-TRANSPLANTION SURVIVAL DATA FOR GRAFTED NT2N CELLS

| Post-transplant survival | Number Of Rats injected w/NT2N Cells | Number Of Rats with viable NT2N cell grafts |
|---|---|---|
| ADULT UNTREATED RATS | | |
| 4 Days | 3 | 3 |
| 2 Weeks | 2 | 2 |
| 4 Weeks | 24 | 10 |
| 6 Weeks | 4 | 0 |
| 8 Weeks | 3 | 1 |
| 13 Weeks | 2 | 0 |
| SUBTOTAL = 38 | | SUBTOTAL = 16 |
| NEONATAL UNTREATED RATS | | |
| 1 Week | 2 | 2 |
| 2 Weeks | 3 | 3 |
| 4 Weeks | 2 | 2 |
| 8 Weeks | 2 | 0 |
| 12 Weeks | 2 | 0 |
| 16 Weeks | 2 | 0 |
| 16 Weeks | 2 | 0 |
| 21 Weeks | 2 | 0 |
| SUBTOTAL N = 17 | | SUBTOTAL N = 7 |
| ADULT CYCLCSPORINE TREATED RATS | | |
| 2 Weeks | 3 (sc = 1) | 3 (sc = 1) |
| 4 Weeks | 1 (sc) | 1 |
| 6 Weeks | 1 (sc) | 1 |
| 8 Weeks | 2 (sc = 1) | 1 (sc = 1) |
| 10 Weeks | 2 | 0 |
| 11 Weeks | 3 | 0 |
| 12 Weeks | 1 (sc) | 1 |
| SUBTOTAL = 13 | | SUBTOTAL = 7 |
| GRAND TOTAL = 68 | | GRAND TOTAL = 30 |

TABLE 2

POLYPEPTIDE AND CELL SPECIFICITY OF ANTIBODIES AND THEIR REACTIVITY WITH GRAFTED NT2N CELLS

| POLYPEPTIDE | ANTIBODY | DILUTION µg/ml | NT2N GRAFT |
|---|---|---|---|
| NEURONS | | | |
| Clathrin light chain | LCB2 | 0.1 | +/− |
| MAP2 | AP14 | 1:100 | + |
| MAP5 | AA6 | 1:1500 | + |
| NF-H, P+++ | RMO24 | Neat | − |
| NF-H, P+++ | RMO217 | Neat | − |
| NF-H, P+ | TA51 | 1:20 | + |
| NF-H/M, P− | RMdO020 | 1:10 | + |
| NF-H, P++ | HO14 | 1:25 | + |
| NF-M, P$^{ind}$ | RMO254 | 1:25 | + |
| NF-L, P$^{ind}$ | NR 4 | 1:10 | + |
| NF-L, P$^{ind}$ | Anti-NF-L | 1:50 | + |
| Neuron Specific Protein | NST11 | 1:10 | − |
| Protein Kinase C$_\gamma$ | PKC66 | Neat | − |
| Tau | T14 | Neat | + |
| Tau | 134 | 1:500 | +/− |
| Tau (fetal/PHF) | T3P | 1:50 | + |
| Tau (fetal/PHF) | PHF1 | 1:2000 | +/− |
| NEURONS AND NEUROENDOCRINE CELLS | | | |
| Chromogranin | LK2h10 | 1:500 | − |
| Synaptophysin | SY 38 | 1:100 | +/− |
| Tyrosine Hydroxlase | Anti-TH | 1:100 | − |
| NEUROEPITHELIAL STEM CELLS | | | |
| Nestin | Anti-Nestin | 1:2000 | − |
| GLIAL CELLS | | | |
| GFAP | 2.2B10 | 1:500 | − |
| MBP | Anti-MBP | 1:100 | − |
| NEURAL, MESENCHYMAL & OTHER CELLS | | | |
| N-CAM | MOC 1 | 1:10 | + p75 |
| NGFR | Me 20.4 | 1:100 | − |
| Vimentin | V9 | 1:100 | − |
| Macrophage marker | ED1 | 1:500 | − |

We claim:

1. A composition comprising:
   a sample of cells from a culture of at least 95% pure, stable, homogeneous post-mitotic human differentiated NT2N neurons; and
   a pharmaceutically acceptable medium.

2. The composition of claim 1 wherein said neurons have been transfected with exogenous genetic material so that said transfected neurons express coding sequences of said exogenous genetic material to produce a protein product in said neurons.

3. The composition of claim 1 wherein said exogenous genetic material comprises nucleic acid sequences that encode a protein selected from the group consisting of a protein neurotransmitter and a neurotropin.

4. The composition of claim 1 wherein the neurotropin is selected from the group consisting of nerve growth factor, brain derived neurotrophic factor, basic fibroblast growth factor and glial-derived growth factor.

5. A method of generating a rodent useful for studies of the developmental biology of neurons and regressive neurological events that occur in some neurological disorders comprising the step of:
   implanting post-mitotic human NT2N neurons into said rodent's brain; wherein said implanted neurons integrate and survive within the brain of said rodent.

6. The method of claim 5 wherein said implanted neurons have been transfected with exogenous genetic material so that transfected cells express coding sequences of said exogenous genetic material to produce a protein product in said neurons.

7. The method of claim 6 wherein said exogenous genetic material includes nucleic acid sequences that encode proteins selected from the group consisting of an amyloid precursor protein, a kinase, a phosphatase, a superoxide dismutase, a neurofilament protein, and apolipoprotein 4.

8. The method of claim 5 wherein said rodent is an immunocompetent rodent and further comprising the step of administering Cyclosporin to said immunocompetent rodent before, during and/or after implanting said cells.

9. A chimeric rodent wherein said rodent comprises post-mitotic human NT2N neurons stably implanted in the brain of said rodent.

10. The rodent of claim 9 wherein said neurons have been transfected with exogenous genetic material so that said transfected neurons express coding sequences of said exogenous genetic material to produce a protein product in said neurons.

11. The rodent of claim 9 wherein said exogenous genetic material includes nucleic acid sequences that encode proteins selected from the group consisting of an amyloid precursor protein, a kinase, a phosphatase, a superoxide dismutase, a neurofilament protein, and apolipoprotein 4.

* * * * *

UNITED STATES PATENT AND TRADEMARK OFFICE
CERTIFICATE OF CORRECTION

PATENT NO. : 5,792,900
DATED : August 11, 1998
INVENTOR(S) : Lee and Trojanowski It is certified that error appears in the above-identified patent and that said Letters Patent are hereby corrected as shown below:

Col 3, line 66, please delete "CDNA" and insert therfor --cDNA--
Col 10, line 42, please delete "±-weak and insert therefor --+/--weak--
Col 12, line 20, please delete "(MOCL) and insert therfor --(MOC1)--

Signed and Sealed this

Twelfth Day of January, 1999

Attest:

Attesting Officer     *Acting Commissioner of Patents and Trademarks*